United States Patent
Bohner et al.

(10) Patent No.: US 6,733,582 B1
(45) Date of Patent: May 11, 2004

(54) BRUSHITE HYDRAULIC CEMENT STABILIZED WITH A MAGNESIUM SALT

(75) Inventors: Marc Bohner, Zürich (CH); Sandro Matter, Aarau (CH)

(73) Assignees: Dr. H. C. Robert Mathys Stiftung, Bettlach (CH); Stratec Medical AG, Oberdorf (DE)

( * ) Notice: Subject to any disclaimer, the term of this patent is extended or adjusted under 35 U.S.C. 154(b) by 0 days.

(21) Appl. No.: 10/149,035

(22) PCT Filed: Dec. 9, 1999

(86) PCT No.: PCT/CH99/00595

§ 371 (c)(1),
(2), (4) Date: Jul. 2, 2002

(87) PCT Pub. No.: WO01/41824

PCT Pub. Date: Jun. 14, 2001

(51) Int. Cl.$^7$ .......................... C04B 28/30; C04B 28/34
(52) U.S. Cl. ......................... 106/690; 106/691
(58) Field of Search .................. 106/690, 691

(56) References Cited

U.S. PATENT DOCUMENTS

| 5,152,836 A | | 10/1992 | Hirano et al. | |
|---|---|---|---|---|
| 5,605,713 A | | 2/1997 | Boltong | |
| 5,900,254 A | * | 5/1999 | Constantz | 424/602 |
| 6,053,970 A | * | 4/2000 | Ison et al. | 106/35 |

OTHER PUBLICATIONS

WO 99/17710, Hydraulic Surgical Cement, Publication Date: Apr. 15, 1999, Applicant: Dr. H.C. Robert Mathys Stiftung and Stratec Medical AG.

Driessens et al.: "Effective formulations for the preparation of calcium phosphate bone cements", Journal of Material Science: Materials in Medicine, vol. 5, 1994, pp. 164–170, XP000929539.

* cited by examiner

Primary Examiner—Elizabeth D. Wood
(74) Attorney, Agent, or Firm—Rankin, Hill, Porter & Clark LLP

(57) ABSTRACT

A brushite cement for surgical purposes includes a first component including a basic calcium phosphate, a second component including an acidic phosphate, a third component including water, and a fourth component including a source of magnesium used to stabilize an end-product of the setting reaction between the components. The solubility of the source of magnesium is smaller than 100 g/L. The components are chosen in such an amount that (i) the pH of the cement past during setting is lower than 6.0; and (ii) the end-product of the setting reaction comprises dicalcium phosphate dihydrate.

50 Claims, No Drawings

BRUSHITE HYDRAULIC CEMENT STABILIZED WITH A MAGNESIUM SALT

BACKGROUND OF THE INVENTION

This invention concerns a cement for surgical purposes, a method for stabilizing a brushite cement used as temporary bone replacement material and the temporary bone replacement material obtained by said method.

A number of such hydraulic cements based on calcium phosphates for use in surgery are known in the prior art; they are prepared from two components (powder/liquid) by mixing them intraoperatively and applying them in pasteous consistency to the appropriate site where they harden in situ. The disadvantages of the prior art hydraulic cements based calcium phosphates are:

a) impracticable short setting times which do not allow their use for elaborate surgical procedures;

b) poor injectability, i.e. the fresh cement paste tends to clog the injection needle, and/or disintegrates in contact with physiological liquids, which prevents its implantation by minimal invasive surgery procedures;

c) low compacity, i.e. current hydraulic cements need larger amounts of mixing water in order to have them injectable or to confer them a convenient setting time, which results in very low ultimate mechanical strength after hardening; and d) too fast resorption, i.e. the cement resorbs faster than the bone growth rate, resulting in a non-osseous gap between bone and cement which is detrimental to the mechanical properties of the cement.

In the U.S. Pat. No. 4,880,610 CONSTANTZ a method is disclosed for making an in situ calcium phosphate mineral composition by combining water-free phosphoric acid crystals with a calcium source which leads to a hydroxyapatite. It is clear that the use of 100% phosphoric acid in the operating room and the application of a paste containing 100% phosphoric acid in the human body must be considered a not ideal procedure which requires improvement.

In U.S. Pat. No. 5,129,905 CONSTANTZ—in order to reduce the problem—phosphoric acid crystals were replaced by monocalcium phosphate monohydrate (MCPM) or monocalcium phosphate (MCP). However, the goal was again to obtain a hydroxyapatite material, which has a long resorption period. A long resorption period is not commensurate to the rate of the bone remodelling. The disadvantage of prolonged resorption is that the bone treated by cement will remain for a prolonged time in abnormal biomechanical situation, which may develop secondary post-operational problems. Furthermore, the unresorbed cement may still break down in pieces or fragments after prolonged mechanical loading, which increases the probability of post-operational complications, e.g. aseptic inflammatory reactions. The resorption rate of the ideal cement should match as closely as possible the spontaneous rate of new bone formation which is around 20 micrometers per day. A too fast resorption rate is also not wanted. Certain studies done with plaster of Paris and calcium phosphate cement have shown that the resorption rate is faster than the bone growth rate, leading to a gap between bone and cement. This is obviously detrimental to the mechanical stability of the defect site.

From U.S. Pat. No. 5,605,713 BOLTONG a calcium phosphate composition is known which may contain (among others) β-TCP, MCPM, water and magnesium salts. However, the invention is limited to pH values in the range of 6.5 to 8.0, range in which brushite does not precipitate. A pH below 6,5 preferably below 4 is needed to obtain brushite. In the pH range of 6.5 to 8.0, octocalcium phosphate and hydroxyapatite are the phases precipitating. However, these phases are much less soluble than brushite at neutral pH and thus lead to too slow resorption rates.

From PCT/EP98/06330 a calcium phosphate composition is known which contains brushite (dicalcium phosphate dihydrate; $CaHPO_4 \cdot 2H_2O$) as end-product of the setting reaction. This cement has however a too fast resorption rate in vivo, leading to mechanical instabilities and inflammatory reactions.

SUMMARY OF THE INVENTION

The invention as claimed aims at solving the above described problems. The present invention provides a cement for surgical purposes, a method for producing a temporary bone replacement material as defined and a temporary bone replacement material.

The various features of novelty which characterize the invention are pointed out with particularity in the claims annexed to an forming part of this disclosure. For the better understanding of the invention, its operating advantages and specific objects attained by its use, reference should be done to the accompanying examples in which preferred embodiments of the invention are illustrated in detail.

The first component of the cement according to The invention comprises a basic calcium phosphate, preferably β-tricalcium phosphate [$\beta$-$Ca_3(PO_4)_2$; β-TCP], α-tricalcium phosphate [$\alpha$-$Ca_3(PO_4)_2$; α-TCP], tetracalcium phopshate $Ca_4(PO_4)_2O$; TetCP], oxyapatite $Ca_{10}(PO_4)_6O$; OXA], hydroxyapatite [$Ca_5(PO_4)_3OH$; HA], or calcium-deficient hydroxyapatite [$Ca_{10-x}(HPO_4)_x(PO_4)_{6-x}(OH)_{2-x}$; CDHA] powder. It can also be a mixture of two or three of the latter compounds. β-TCP is the preferred compound.

The second component of the cement according to the invention comprises an acidic calcium phosphate, preferably monocalcium phosphate monohydrate [$Ca(H_2PO_4)_2 \cdot H_2O$; MCPM], monocalcium phosphate [$Ca(H_2PO_4)_2$; MCP], or phosphoric acid [$H_3PO_4$] powder. It can also be a mixture of two or three of the latter compounds. MCPM is the preferred compound.

The third component of the cement according to the invention comprises water.

The fourth component of the cement according to the invention comprises a source of magnesium used to stabilize the end-product of the setting reaction.

DETAILED DESCRIPTION OF THE PREFERRED EMBODIMENTS

The setting reaction is characterized by several partial reaction: dissolution of the first component, dissolution of the second component and precipitation of the end-product of the setting reaction, i.e. brushite (dicalcium phosphate dihydrate; $CaHPO_4 \cdot H_2O$). Normally, the dissolution reaction of the second component is much faster than that of the first component. As the second component is acidic, the cement paste reaches pH values of 2 to 4 depending on the cement composition and particle size distribution. When the second component is completely dissolved, the ongoing dissolution of the first component, which is basic, provokes an increase of the pH value of the cement paste. However, the pH of the cement according to the invention at the end of the setting reaction is always in the range of 2 to 6. It is also in this range that brushite preferentially precipitates. At higher pH values (6 and higher), brushite does not precipitate: octocalcium phosphate and hydroxyapatite are the phases precipitating. However, these phases are much less soluble than brushite at neutral pH and would thus lead to too slow resorption rates.

The particular size distribution and the mean specific surface area of the solid components has a large influence on the physico-chemical properties of the cement, in particular the setting time, the mechanical properties, and the workability. Generally speaking, powders with a high specific surface area lead to short setting times, high mechanical-properties, and good workability. However, this rule is no more valid when the powders are agglomerated: a large amount of mixing liquid is required to water the powders, hence leading to poor mechanical properties. Therefore, powders should preferably be desagglomerated.

A good workability depends very much on the application. In some cases, a rather liquid paste is desired (reinforcement of osteoporotic bones). In other cases, a very thick paste may be the most adequate (e.g. plastic surgery). A powder with a small average particle size possess only a very small range in which a paste can be formed with water the paste is either solid and breakable, or very liquid. Generally, a thick paste is preferred, because the paste is more easily workable and remains stable upon contact with body fluids. So a paste containing powders with a large average particle size is normally chosen. A typical range for the mean particle size of the powders is 0.1 to 100 micrometers.

The solubility of the different solid components has a large influence on the cement setting time. If the first component is very soluble, the setting reaction is fast. If the first component is poorly-soluble, the setting reaction tends to be slow. For example, the use of the very soluble α-TCP or TetCP powder as first component leads to very short setting times. The use of the rather soluble β-TCP powder as first component leads to short setting times. Finally the use of the rather insoluble HA, CDHA or OXA powder leads to long setting times. So, in order to obtain a setting time in the order of 5 to 20 minutes, it is desirable to use a β-TCP powder with a small specific surface area, and a CDHA or HA powder with a large specific surface area. Assuming that the powders are desagglomerated, a typical range for the mean particle size of the powders is 0.1 to 1 micrometers for CDHA, OXA, or HA powder, 1 to 10 micrometers for β-TCP powder, and 5 to 100 micrometers for α-TCP or TetCP powder.

Despite the use of large α-TCP, TetCP, and/or β-TCP particles, the setting time of a cement containing α-TCP, TetCP, and/or β-TCP as first component is normally too short. Setting time of the cement according to this invention as measured at 25° C. should preferably be at least 1 minute, typically at least 2 minutes and preferably at least 5 minutes. So, a setting rate controller is normally used. It is chosen from the group of sodium pyrophosphate, potassium pyrophosphate, sodium acetate, potassium acetate, sodium citrate, potassium citrate, sodium phosphocitrate, potassium phosphocitrate, sodium sulfate, potassium sulfate, calcium sulphate hemihydrate, sodium pyrophosphate, sodium dihydrogen pyrophosphate, magnesium sulfate and sodium or potassium biphosphonate. The setting rate controller can be added either pre-dissolved in the third component or as a solid (powder). However, in the latter case, the setting rate; controller must be very soluble, so that the solid dissolves almost instantaneously upon contact with water. Sodium pyrophosphate and sodium sulfate are normally the preferred setting rate controllers. If HA, OXA, or COHA are used as first component, the setting time is normally too long. The setting time can be decreased by adding appropriate setting rate controllers. Efficient setting rate controllers are compounds containing orthophosphate ions such as sodium, magnesium or potassium orthophosphate salts, or phosphoric acid.

The third component comprising water may further comprise phosphoric acid (OPA) and/or sulfuric acid (SA), which again take the function of a setting rate controller and also lead to an improved microstructure of the final brushite crystals.

To control the resorption rate of the cement, granules having an average diameter which is larger than the average diameter of said first component can be added. This leads to conglomerate structure of the finally set cement, whereby the granules are embedded in the brushite matrix formed by the setting process. The average particle diameter of the latter granules should be at least two times larger, preferably at least 10 times larger compared with the average diameter of the particles of the first component. The average particle diameter of said granules should be in the range of 50 to 2000 micrometers. Preferably, it should be in the range of 100 to 500 micrometers, preferably in the range of 200 to 350 micrometers. The granules may consist of calcium phosphates, e.g. α-TCP, TetCP, OXA, β-TCP, HA, CDHA, biphasic calcium phosphate (BCP), gypsum, bioglass, and polymers, e.g. lactides, polysaccharides, collagen, proteins. The preferred composition for these granules is β-TCP. The advantage of using granules is the differential degradation of such a cement. The matrix of the cement is degraded faster or slower than the residual granulates. This is particularly useful for the application in the osteoporose field or for ridge reconstruction of the jaw, where a slower degrading granule, e.g. made from hydroxyapatite or BCP is desired. The use of a fast resorbable granule (e.g. gypsum) may allow the obtention of a macroporous cement structure after a short implantation time.

The volume $V_L$ of the third component should preferably be equal or superior than the volume $V_T=(W_{MCPA} \times 0.615 + W_{MCPM} \times 0.5 + W_{OPA} \times 1.102 + W_{SA} \times 1.101)$ ml/g of the second component, where $W_{MCPA}$, $W_{MCPM}$, $W_{OPA}$, and $W_{SA}$ are the weight of MCP, MCPM, phosphoric acid and sulfuric acid, respectively. The volume $V_L$ is typically in the range of $0.5 \times V_T \leq V_L \leq 10 \times V_T$, preferably in the range of $1.2 \times V_T + \leq V_L \leq 2.5 \times V_T$. The amount of mixing liquid (third component) has a strong influence on the physico-chemical properties of the cement, in particular the setting time, and the mechanical properties. The setting time and the cement porosity increase with an increase of $V_L$. As the mechanical properties are decreased by an increase of porosity, an optimum for $V_L$ can be chosen regarding setting time and mechanical properties.

To optimize the cement compatibility in vivo, the cement should contain an excess of basic components, i.e. an excess of the first component compared with the second component. In other words, the Ca:P molar ratio of the cement must be superior or equal to 1.0. The Ca:P molar ratio can be written (assuming that x=1 in CDHA ($Ca_{10-x}(HPO_4)_x (PO_4)_{6-x}(OH)_{2-x}$)):

Ca:P ratio=$(W_{MCP}/236+W_{MCPM}/252+3 \times W_{TCP}/310+4 \times W_{TetCP}/366+10 \times W_{OXA}/986+5 \times W_{HA}/502+9 \times W_{CDHA}/948)/(2 \times W_{MCP}/236+2 \times W_{MCPM}/252+2 \times W_{TCP}/310 \times 2 \times W_{TetCP}/366+6 \times W_{OXA}/986+3 \times W_{HA}/502+6 \times W_{CDHA}/948+W_{OHA}/98)$ where $W_{MCP}$, $W_{MCPM}$, $W_{TCP}$, $W_{HA}$, $W_{CDHA}$ and $W_{OHA}$ are the weight of MCP, MCPM, α or β-TCP, TetCP, OXA, HA, CDHA and phosphoric acid respectively. The preferred Ca:P molar ratio lies in the range of 1.00 to 1.67, preferably in the range of 1.05 to 1.30.

One of the four components may further comprise a biodegradable polymer for controlling the consistency of the cement paste resulting from mixing of the two components, and its cohesion in physiological liquids. There are two goals in controlling the cement consistency: (i) by increasing the viscosity of the mixing liquid, the paste becomes less sensitive to filter-pressing (no demixing during injection); and (ii) by increasing the viscosity of the mixing liquid, the viscosity of the cement paste is increased and the cement paste does not decompose when put into an aqueous solution.

The biodegradable polymer may be selected from the group of hyaluronic acid, hyaluronatesalts, dextran, alginate, hydroxypropylmethyl cellulose, chitosan, xanthan gum, agarose, polyethylene glycols (PEG), polyhydroxyethylenemethacrytats (HEMA), synthetic and natural proteins, or collagen.

The cement may further comprise pharmaceutically or physiologically active substances, preferably selected from the group of antibiotics, anti-inflammatory drugs, anti-cancer drugs, peptides, and proteins such as growth factors. The antibiotic is preferably a gentamicin or a gentamicin salt, typically gentamicin sulfate. Other gentamicin salts can be used provided their solubility is in the range of 100 to 2500 mg/L.

The antibiotic is selected from the group of aminoglycosides, vancomicins, gentamicins or salts thereof, preferably gentamicin sulfate or gentamicin crobefat.

The cements according to the invention may be used as bons substitute in dental and maxillofacial surgery (alveolar ridge reconstruction, dental socket filling), for orthopaedic applications (bone fracture repair, bone augmentation) and for local drug delivery (antibiotics, anti-inflammatory and anti-cancer drugs).

The third component of the cement may further comprise a hydrophobic liquid that can act either as a lubricant or as a pore forming agent. In the latter case, the cement mixture is stirred mechanically until an emulsion is obtained. The paste can then be injected. After setting, the hydrophobic liquid is entrapped in the cement matrix, hence forming pores. The emulsion can be stabilized by means of an emulsifier. The hydrophobic liquid and the emulsifier should be preferably chosen for in vivo implantation. Compounds of choice are all natural products.

The fourth component of the cement is taken from the group of $MgO$, $MgO_2$, $Mg(OH)_2$, $MgHPO_4$, $MgHPO_4 \cdot 3H_2O$, $MgHPO_4 \cdot 7H_2O$, $Mg_3(PO_4)_2$, $Mg_3(PO_4)_2 \cdot 4H_2O$, $Mg_3(PO_4)_2 \cdot 8H_2O$, $Mg_3(PO_4)_2 \cdot 22H_2O$, $MgCO_3$, $MgCO_3 \cdot 3H_2O$, $MgCO_3 \cdot 5H_2O$, $3MgCO_3 \cdot Mg(OH)_2 \cdot 3H_2O$, $MgCO_3Mg(OH)_2 \cdot 3H_2O$, $Mg(C_3H_5O_3)_2 \cdot 3H_2O$, $MgC_2O_4 \cdot 2H_2O$, $MgC_4H_4O_6 \cdot 5H_2O$, $Mg(C_4H_4O_6)_2 \cdot 4H_2O$, $MgCO_3 \cdot CaCO_3$, $Mg_2P_2O_7$, $Mg(C_{12}H_{23}O_2)_2 \cdot 2H_2O$, $Mg(C_{14}H_{27}O_2)_2$, $Mg(C_{18}BH_{33}O_2)_2$, $Mg(C_{18}H_{35}O_2)_2$. The amount of the fourth component should be comprised in the range of 0.001 to 60% w/w, more precisely in the range of 1 to 20% w/w, preferably in the range of 2 to 5% w/w. The magnesium salt should not be too soluble to prevent a fast release of Mg ions from the implant site. The solubility in water should preferably be lower than 10 g/L and more preferably lower than 1 g/L.

Five specific examples are reported below for producing the temporary bone replacement materials according to the invention.

EXAMPLE 1

Samples with various cement compositions were prepared. The cement composition was: 1.33 g β-TCP (mean particle diameter in volume: 1.1 micrometer), 0.67 g MCPM, 25 mg $Na_2H_2P_2O$, 1 g TCP granules (400 to 500 micrometers in diameter) and (x) mg $Na_2SO_4$ or $MgSO_4$. The mixing liquid was 1 g of an aqueous hyaluronic acid solution (viscosity: 200 mPa·s). Three repeats were made. The samples were prepared as follow: (i) 30 s mixing of the powders with the solution, (ii) insertion of the paste into the tip of a cement syringe, (iii) measurement of the setting time, (iv) ejection of the sample out of the syringe, (v) aging in 2 mL d.i. water for 24 hours, (vi) drying. To measure the pH, a sample of each composition was placed into 10 mL d.i. water and the pH was measured at regular intervals. The tensile strength of the samples was determined by means of the Brazilian tensile test The crystalline composition of the samples was determined by x-ray diffraction (XRD). Results showed that the setting time increased drastically at a sulfate concentration of 0.1M: from 3 minutes to 15 minutes. Interestingly, the setting time was a little bit longer with magnesium ions than with sodium ions (about 1 minute longer above a concentration of 0.15M). The mechanical properties were not significantly modified by the addition of sodium or magnesium sulfate. However, a sulfate concentration superior to 0.1M led to finer microstructures. The end-product of the reaction was brushite.

EXAMPLE 2

Cement samples were prepared according to a factorial design of experiments $2^3$ with 4 repeat. The factors were: (A) Sulfate source ($Na_2SO_4$ or $MgSO_4$); (B) Sulfate amount (20 or 50 mg) and (C) $Ca_2P_2O_7$ amount (0/150 mg). The cement composition was: 1.33 g β-TCP (mean particle diameter in volume: 1.1 micrometer), 0.67 g MCPM, 25 mg $Na_2H_2P_2O_7$, 1 g TCP granules (400 to 500 micrometers in diameter), 20 or 50 mg $Na_2O_4$ or $MgSO_4$, and 0 or 150 mg $Ca_2P_2O_7$. The mixing liquid was 1 g of an aqueous hyaluronic acid solution (viscosity: 200 mPa·s). The samples were prepared and analyzed as explained in the first example. Results show that the setting time of the cement was significantly increased by replacing sodium sulfate with magnesium sulfate, and significantly decreased when $Ca_2P_2O_7$ was added to the cement paste. The latter effect is due to the fact that the powder/liquid ratio was increased. The amount of sulfate ions did only play a minor role at the chosen concentration: the setting time was slightly increased by an increase of sulfate amount. This result is actually similar to what was observed in the first example. The cement tensile strength was decreased when $Na_2SO_4$ was replaced by $MgSO_4$, and when $Ca_2P_2O_7$ or more sulfate were added to the cement. The cement microstructure was finer with 50 mg sulfate salt than with only 20 mg.

EXAMPLE 3

Cement samples were prepared by mixing for 60 seconds with a spatula the cement powder with the mixing liquid. Afterwards, the paste was poured into a syringe and the paste was injected with the syringe into a cylindrical defect (8 mm diameter) made in the proximal or distal femora/humerus of a sheep. Eight compositions were tested pro sheep according to the factorial design of experiment: (A) Sulfate source ($Na_2SO_4$ or $MgSO_4$); (B) $MgHPO_4 \cdot 3H_2O$ (0/150 mg) and (C) $Ca_2P_2O_7$ amount (0/150 mg). The cement composition was: 5.33 g β-TCP (mean particle diameter in volume: 1.1 micrometer), 2.66 g MCPM, 100 mg $Na_2H_2P_2O_7$, 4 g TCP granules (400 to 500 micrometers in diameter), 100 mg $Na_2SO_4$ or $MgSO_4$, 0 or 600 mg $MgHPO_4 \cdot 3H_2O$, and 0 or 600 mg $Ca_2P_2O_7$. The mixing liquid was 4 mL of an aqueous hyaluronic acid solution (viscosity: 200 mPa·s). Two sheep were operated. The first sheep was killed after 3 weeks. The second after 6 weeks. Results showed that all the samples which did not contain $MgHPO_4 \cdot 3H_2O$ decomposed much quicker than the other. Moreover, after three week implantation, the samples which did not contain $MgHPO_4 \cdot 3H_2O$ had provoked a large inflammatory reaction and partial disappearance of the bone surrounding the implant. Fibrous tissue was found between the implant and bone. In conclusion, it resulted that the presence of a poorly-soluble salt like $MgHPO_4 \cdot 3H_2O$ is necessary to improve the in vivo behavior of brushite cement.

EXAMPLE 4

Cement samples were prepared by mixing for 60 seconds with a spatula the cement powder with the mixing liquid. Afterwards, the paste was poured into a syringe and the paste was injected with the syringe into a cylindrical defect (8 mm diameter) made in the proximal or distal femora/humerus of a sheep. Three compositions and one control (empty hole) were tested pro sheep. The first composition was a commercial product, Norian SRS, which contains as end-product a poorly-crystallized carbonato-apatite. Second composition: 0.96 g β-TCP (mean particle diameter in volume: 1.1 micrometer), 1.92 g MCPM, 80 mg $Na_2H_2P_2O_7$, 6.72 g TCP granules (125 to 1000 micrometers in diameter), 100 mg $Na_2SO_4$, 600 g $CaSO_4 \cdot 1/2H_2O$, and 600 mg $Ca_2P_2O_7$. The mixing liquid was 4 mL of an aqueous hyaluronic acid solution (viscosity: 200 mPa·s). The third cement composition was: 5.33 g HA (mean particle diameter in volume: 0.08 micrometer), 2.66 g MCPM, 20 mg $Na_2H_2P_2O_7$, 4 g TCP granules (125 to 1000 micrometers in diameter), 100 mg $Na_2SO_4$, and 600 mg $Mg_2P_2O_7$. The mixing liquid was 6 mL of an aqueous xanthan solution (viscosity: 100 mPa·s). Two sheep were operated. The first sheep was killed after 3 weeks. The second after 6 weeks. Norian SRS cement behaved like an inert material. No resorption could be observed after 6 week implantation. The second cement provoked a large inflammatory reaction and osteolysis after 3 weeks. Fibrous tissue was present between the cement and bone. After 6 weeks, the situation was similar as after 3 weeks, suggesting that only the early reaction provoked by the presence of the cement was detrimental to the sheep bone. The third cement provoked only a mild inflammatory reaction and no osteolysis could be observed. After 6 weeks, 20% of the third cement had resorbed and been replaced by new bone. There was a direct apposition of new bone on the third cement.

EXAMPLE 5

Cement samples were prepared according to the following composition: 1.2 g HA (mean particle diameter in volume: 2 micrometer), 0.6 g MCPM, 1 g HA granules (200 to 300 micrometers in diameter), and 0 to 0.1 g gentamicin sulfate (powder). The mixing solution (1.2 mL) was a 0.1M aqueous $Na_2HPO_4$ solution containing 0.5 weigth-% xantham gum. The cement was prepared according to the following scheme: (i) thoroughly mixing the different powders with the mixing liquid for 45 seconds; (ii) insertion of the paste into the tip of a syringe, (iii) measurement of the setting time, (iv) ejection of the sample out of the syringe, (v) aging in 2 mL d.i. water for 24 hours, (vi) drying. In some cases, the samples were not aged and dried, but placed in 250 ml PBS 7.4 and the amount of gentamicin released by the cement sample was measured over time. The setting time was influenced by the presence of gentamicin sulfate: the addition of more than about 300 mg gentamicin sulfate increased the setting time by a factor of 2 (4 to 8 minutes). The mechanical properties were also increased by the addition of gentamicin sulfate: between 400 and 500 mg gentamicin sulfate, the tensile strength increased from 3.2 to 5.8 MPa. The release experiments showed that gentatamicin was released according to a first-order reaction from the cement matrix. Small amounts of gentamicin were still released after 5 days.

We claim:

1. A cement for surgical purposes comprising:
 a first component comprising a basic calcium phosphate;
 a second component comprising an acidic phosphate;
 a third component comprising water, and
 a fourth component used to stabilize an end-product of the setting reaction between the components comprising a magnesium salt having a solubility in water less than 100 g/L, wherein:
 the components are chosen in such an amount that:
  (i) the pH of the cement during setting is lower than 6.5; and
  (ii) the end-product of the setting reaction comprises dicalcium phosphate dihydrate.

2. The cement according to claim 1, wherein the first component comprises β-tricalcium phosphate.

3. The cement according to claim 1, wherein the first component comprises α-tricalcium phosphate.

4. The cement according to claim 1, wherein the first component comprises tetracalcium phosphate.

5. The cement according to claim 1, wherein the first component comprises oxyapatite.

6. The cement according to claim 1, wherein the first component comprises hydroxyapatite.

7. The cement according to claim 1, wherein the first component comprises calcium-deficient hydroxyapatite.

8. The cement according to claim 1, wherein the second component comprises monocalcium phosphate monohydrate.

9. The cement according to claim 1, wherein the second component comprises monocalcium phosphate.

10. The cement according to claim 1, wherein the fourth component is present in an amount of 0.001 to 60% w/w.

11. The cement according to claim 10, wherein the fourth component is present in an amount of 1 to 20% w/w.

12. The cement according to claim 11, wherein the fourth component is present in an amount of 2 to 5% w/w.

13. The cement according to claim 1, wherein the fourth component is selected from the group consisting of MgO, $MgO_2$, $Mg(OH)_2$, $MgHPO_4$, $MgHPO_4 \cdot 3H_2O$, $MgHPO_4 \cdot 7H_2O$, $Mg_3(PO_4)_2$, $Mg_3(PO_4)_2 \cdot 4H_2O$, $Mg_3(PO_4)_2 \cdot 8H_2O$, $Mg_3(PO_4)_2 \cdot 22H_2O$, $MgCO_3$, $MgCO_3 \cdot 3H_2O$, $MgCO_3 \cdot 5H_2O$, $3MgCO_3 \cdot Mg(OH)_2 \cdot 3H_2O$, $MgCO_3 \cdot Mg(OH)_2 \cdot 3H_2O$, $Mg(C_3H_5O_3)_2 \cdot 3H_2O$, $MgC_2O_4 \cdot 2H_2O$, $MgC_4H_4O_5 \cdot 5H_2O$, $Mg(C_4H_4O_6)_2 \cdot 4H_2O$, $MgCO_3 \cdot CaCO_3$, $Mg_2P_2O_7$, $Mg(C_{12}H_{23}O_2)_2 \cdot 2H_2O$, $Mg(C_{14}H_{27}O_2)_2$, $Mg(C_{18}H_{33}O_2)_2$, and $Mg(C_{18}H_{35}O_2)_2$.

14. The cement according to claim 1, wherein the fourth component is selected from the group consisting of $MgHPO_4$, $MgHPO_4 \cdot 3H_2O$, $MgHPO_4 \cdot 7H_2O$, $Mg_3(PO_4)_2$, $Mg_3(PO_4)_2 \cdot 4H_2O$, $MgCO_3$, $MgCO_3 \cdot CaCO_3$.

15. The cement according to claim 1, wherein the third component of the cement is selected from the group consisting of sulfuric acid, phosphoric acid, and mixtures thereof.

16. The cement according to claim 1, wherein the cement comprises an additive to control the cement setting time.

17. The cement according to claim 16, wherein the setting time additive is selected from the group consisting of sodium pyrophosphate, potassium pyrophosphate, sodium acetate, potassium acetate, sodium citrate, potassium citrate, sodium phosphocitrate, potassium phosphocitrate, sodium sulfate, potassium sulfate, calcium sulphate hemihydrate, sodium pyrophosphate, sodium dihydrogen pyrophosphate, magnesium sulfate, sodium biphosphonate and potassium biphosphonate.

18. The cement according to claim 16, wherein the setting time additive is selected from the group consisting of sodium orthophosphate and potassium orthophosphate.

19. The cement according to claim 1, wherein the third component of the cement further comprises an additive to control the cement rheology.

20. The cement according to claim 19, wherein the additive used to control the cement rheology is selected from the group consisting of polysaccharide derivatives, hyaluronic acid, hyaluronate salts, dextran, alginate, hydroxypropylmethyl cellulose, chitosan, and xanthan gum.

21. The cement according to claim 19, wherein the additive used to control the cement rheology selected from the group consisting of hyaluronic acid and hyaluronate salts.

22. The cement according to claim 1, wherein a setting time of the cement paste at 25° C. is between about 1 and 20 minutes.

23. The cement according to claim 22, wherein the setting time of the cement paste at 25° C. is between about 2 and 15 minutes.

24. The cement according to claim 23, wherein the setting time of the cement paste at 25° C. is between about 5 and 12 minutes.

25. The cement according to claim 1, wherein a volume VL of the third component is in a range of $0.5\ VT \leq VL \leq 10\ VT$, wherein VT is a powder volume of the cement paste.

26. The cement according to claim 25, wherein the volume VL of the third component is in the range of $1.2\ VT \leq VL \leq 2.5\ VT$.

27. The cement according to claim 1, wherein the cement further comprises granules whose diameter is at least two times larger than the average diameter of particles of the first component.

28. The cement according to claim 27, wherein the granules have an average diameter in the range of 100 μm to 500 μm.

29. The cement according to claim 28, wherein the granules have an average diameter in the range of 200 μm to 350 μm.

30. The cement according to claim 28, wherein the granules are made of calcium phosphate, gypsum, polymer or bioglass.

31. The cement according to claim 28, wherein the granules are made of calcium phosphate and gypsum.

32. The cement according to claim 28, wherein the granules are made of β-TCP.

33. The cement according to claim 1, wherein when the cement hardens, the cement has a Ca:P molar ratio comprised between 1.00 to 1.67.

34. The cement according to claim 33, wherein when the cement hardens, the cement has a Ca:P molar ratio comprised between 1.05 to 1.30.

35. The cement according to claim 1, wherein the cement comprises at least one pharmaceutically or physiologically active substance selected from the group consisting of: antibiotics, anti-inflammatory drugs, anti-cancer drugs, peptides, and proteins.

36. The cement according to claim 1, wherein the cement comprises a hydrophobic liquid.

37. The cement according to claim 36, wherein the cement comprises an emulsifier.

38. The cement according to claim 1, wherein the mixture is injected into a animal or human defect and set in vivo.

39. The cement according to claim 1, wherein the cement comprises a source of strontium ions.

40. The cement according to claim 39, wherein the source of strontium ions is selected from the group consisting of $Sr(C_2H_3O_2)_2$, $Sr(C_2H_3O_2) \cdot 0.5H_2O$, $SrCO_3$, $SrCl_2$, $SrCl_2 \cdot 2H_2O$, $SrCl_2 \cdot 6H_2O$, $SrC_3H_7O_6P$, $Sr(OH)_2$, $Sr(OH)_2 \cdot 8H_2O$, $Sr(C_3H_5O_3)_2 \cdot 3H_2O$, $SrC_2O_4 \cdot H_2O$, $SrHPO_4$, $Sr(HSO_4)_2$, $SrSO_4$, and $SrC_4H_4O_6 \cdot 4H_2O$.

41. The cement according to claim 1, wherein a specific surface area of the first component is in the range of 0.01 to 10 m²/g.

42. The cement according to claim 41, wherein the specific surface area of the first component is in the range of 0.1 to 2 m²/g.

43. The cement according to claim 1, wherein a solubility at 25° C. in water of the fourth component is smaller than 10 g/L.

44. The cement according to claim 43, wherein the solubility at 25° C. in water of the fourth component is smaller than 1 g/L.

45. The cement according to claim 1, wherein the cement contains a radio-opacifiant compound.

46. The cement according to claim 1, wherein the pH value of the cement paste during setting is lower than 6.0.

47. The cement according to claim 46, wherein the pH value of the cement paste during setting is lower than 5.0.

48. A method for producing a matrix of brushite $CaHPO_4 \cdot 2H_2O$ (DCPD) as temporary bone replacement material wherein said first, second, third and fourth components according to claim 1 are mixed together and allowed to harden.

49. A temporary bone replacement material obtained by the method according to claim 48, wherein said material comprises brushite $CaHPO_4 \cdot 2H_2O$ (DCPD).

50. The temporary bone replacement material according to claim 49, further comprising a magnesium salt embedded in said brushite.

* * * * *